(12) United States Patent
Wyrobnik et al.

(10) Patent No.: US 11,166,992 B2
(45) Date of Patent: Nov. 9, 2021

(54) COMPOSITION FOR USE IN THE THERAPY OF LACTOSE INTOLERANCE OR CONDITIONS ARISING FROM LACTASE DEFICIENCY

(71) Applicants: Daniel Henry Wyrobnik, Frankfurt (DE); Isaac Harry Wyrobnik, Frankfurt (DE)

(72) Inventors: Daniel Henry Wyrobnik, Frankfurt (DE); Isaac Harry Wyrobnik, Frankfurt (DE)

(73) Assignee: Vitacare GmbH & Co. KG, Bad Vilbel (DE)

( * ) Notice: Subject to any disclaimer, the term of this patent is extended or adjusted under 35 U.S.C. 154(b) by 464 days.

(21) Appl. No.: 14/703,149

(22) Filed: May 4, 2015

(65) Prior Publication Data

US 2015/0328267 A1    Nov. 19, 2015

Related U.S. Application Data

(63) Continuation of application No. 13/577,392, filed as application No. PCT/EP2011/000510 on Feb. 4, 2011, now abandoned.

(60) Provisional application No. 61/338,763, filed on Feb. 24, 2010.

(30) Foreign Application Priority Data

| Feb. 5, 2010 | (DE) | 102010007142.0 |
| Feb. 8, 2010 | (DE) | 102010007289.3 |
| Feb. 8, 2010 | (DE) | 102010007304.0 |
| Feb. 15, 2010 | (DE) | 102010008083.7 |
| Feb. 26, 2010 | (DE) | 102010009582.6 |
| Apr. 20, 2010 | (EP) | 10004161 |

(51) Int. Cl.
| A61K 35/744 | (2015.01) |
| A61K 35/747 | (2015.01) |
| A61K 38/47 | (2006.01) |
| A61K 35/74 | (2015.01) |

(52) U.S. Cl.
CPC ............ *A61K 35/747* (2013.01); *A61K 35/74* (2013.01); *A61K 35/744* (2013.01); *A61K 38/47* (2013.01); *C12Y 302/01108* (2013.01)

(58) Field of Classification Search
CPC .... A61K 35/747; A61K 35/744; A61K 38/47; C12Y 302/01108
See application file for complete search history.

(56) References Cited

U.S. PATENT DOCUMENTS

| 4,034,115 | A | 7/1977 | Roberts |
| 4,079,125 | A | 3/1978 | Sipos |
| 5,952,021 | A | 9/1999 | Santus |
| 6,008,027 | A | 12/1999 | Langner |
| 6,410,018 | B1 | 6/2002 | Eisenhardt et al. |
| 6,428,786 | B1 | 8/2002 | Eisenhardt et al. |
| 6,562,338 | B2 | 5/2003 | Eisenhardt et al. |
| 6,562,339 | B2 | 5/2003 | Eisenhardt et al. |
| 2005/0100535 | A1 | 5/2005 | Farmer et al. |
| 2006/0068075 | A1* | 3/2006 | Fultz ............... A23C 9/13 426/583 |
| 2006/0263344 | A1 | 11/2006 | Skop et al. |
| 2007/0178213 | A1* | 8/2007 | Ketchmark ......... A23C 9/1307 426/583 |
| 2008/0126195 | A1* | 5/2008 | Ritter ................. A61K 31/7016 705/14.14 |
| 2008/0187525 | A1 | 8/2008 | Porubcan |
| 2008/0213320 | A1 | 9/2008 | Eisenstein et al. |
| 2008/0260708 | A1 | 10/2008 | Hall |
| 2009/0098087 | A1 | 4/2009 | Manzo et al. |
| 2009/0110674 | A1 | 4/2009 | Loizou |

FOREIGN PATENT DOCUMENTS

| DE | 2725731 A1 | 12/1978 |
| DE | 69505374 T2 | 5/1999 |
| DE | 69535290 T2 | 6/2007 |
| DE | 102010009582 A1 | 8/2011 |
| EP | 1112002 B1 | 7/2001 |

(Continued)

OTHER PUBLICATIONS

Mater et al., FEMS Microbiol, Let., *Streptococcus thermophilus* and *Lactobacillusdelbrueckii* subsp. *bulgaricus* survive gastrointestinal transit of healthy volunteers consuming yogurt, 250:185-187 (2005) (Year: 2005).*

(Continued)

*Primary Examiner* — Renee Claytor
*Assistant Examiner* — Trent R Clarke
(74) *Attorney, Agent, or Firm* — Heslin Rothenberg Farley & Mesiti P.C.

(57) ABSTRACT

The invention provides a composition for use in therapy of lactose intolerance or conditions arising from lactase deficiency, wherein the composition is a non-dairy solid dosage form comprising:

(a) a lactase; and (b) one or more lactase-producing and/or lactase containing microorganisms selected from *Lactobacillus delbrueckii* ssp *bulgaricus* and *Streptococcus thermophilus*; wherein the lactase (a) is other than a lactase derived from the said one or more microorganisms (b); and wherein the one or more lactase-producing and/or lactase-containing microorganisms (b) are in dried form.

Also provided are uncoated capsule and tablet compositions containing the lactase and the lactase-producing and/or lactase-containing microorganisms.

22 Claims, No Drawings

(56) References Cited

FOREIGN PATENT DOCUMENTS

| | | |
|---|---|---|
| RU | 2292145 C2 | 1/2007 |
| WO | 95/34292 A2 | 12/1995 |
| WO | 9606924 A1 | 3/1996 |
| WO | 00/10582 A2 | 3/2000 |
| WO | 00/13526 A1 | 3/2000 |
| WO | 2004/089290 A2 | 10/2004 |
| WO | 2009/056979 A1 | 5/2009 |

OTHER PUBLICATIONS

De Vrese et al., Clin. Nutr., 34:394-399 (2015) (Year: 2015).*
Guarner et al; "Should yughurt cultures be considered probiotic?" British Journal of Nutrition (2005). 93, pp. 783-786.
Hove et al; "Effect of lactic acid bacteria on the intestinal production of lactate and short-chain fatty acids, and the absorption of lactose 1-3," American Journal of Clinical Nutrition, 1994, vol. 59, pp. 74-79.
Shah N et al; "Survival of Lactic Acid Bacteria and Their Lactases Under Acidic Conditions," Journal of Food Science, vol. 55, No. 2, 1990, pp. 506-509.
International Search Report for PCT/EP2011/000510 dated Jun. 7, 2011.
EPO Search Report for European Patent Application No. 10004161.5 dated Jun. 29, 2010.
Fernandes et al; J. Appl. Nutr., 41 (1989), 50-64.
Conway et al., J. Dairy Science, 70-1 (1987).
R. Fuller, Journal of Applied Bacteriology, 1989, 66, 365-378.
Newcomer, A.D., et al., "Response of patients with irritable bowel syndrome and lactase deficiency using unfermented acidophilus milk", *The American Journal of Clinical Nutrition,* vol. 38, pp. 257-263 (1983).
Saltzman, J.R., et al., "A randomized trial of Lactobacillus acidophilus BG2FO4 to treat lactose intolerance", *The American Journal of Clinical Nutrition,* vol. 69, pp. 140-146 (1999).

* cited by examiner

COMPOSITION FOR USE IN THE THERAPY OF LACTOSE INTOLERANCE OR CONDITIONS ARISING FROM LACTASE DEFICIENCY

CROSS REFERENCE TO RELATED APPLICATIONS

This application is a continuation of U.S. application Ser. No. 13/577,392 filed on Aug. 6, 2012, which was a national stage filing under section 371 of International Application No. PCT/EP2011/000510, filed on Feb. 4, 2011, and published in English on Aug. 11, 2011 as WO 2011/095339, and claims priority to: U.S. Provisional Application No. 61/338,763, filed on Feb. 24, 2010; German Application No. 10 2010 007 142.0, filed on Feb. 5, 2010; German Application No. 10 2010 007 289.3, filed on Feb. 8, 2010; German Application No. 10 2010 007 304.0, filed on Feb. 8, 2010; German Application No. 10 2010 008 083.7, filed on Feb. 15, 2010; German Application No. 10 2010 009 582.6, filed on Feb. 26, 2010; and European Application No. 10004161.5, filed on Apr. 20, 2010. The entire contents of each of the prior applications are hereby incorporated herein by reference.

The subject matter of the invention is an agent for use in administering to subjects suffering from lactose intolerance, which contains the enzyme lactase (syn. tilactase, tilactasum, beta-galactosidase) in combination with microorganisms. In the context of this patent application, the term lactose intolerance is used to mean not only the medically defined lactose intolerance and lactose metabolism disorder (lactose malabsorption, lactose maldigestion), but any form of health impairments and symptoms that occur as a result of the intake of lactose or lactose-containing foodstuffs, or due to the release of lactose in the digestive tract of humans or animals from other substances, such as pharmaceutical compositions.

BACKGROUND OF THE INVENTION

Lactose is a disaccharide and is an important energy-supplying nutritional component. It occurs as a component primarily in milk and dairy products, but is also used by the food industry as a sweetener, bulking agent and consistency improver, e.g. in sweets, processed meats, bakery products and ready meals. Pharmaceutical compositions also often contain lactose. In the body, lactose is cleaved into the utilisable nutrients glucose and galactose in the small intestine by the endogenous enzyme lactase. For babies, the lactose contained in breast milk is a very important nutrient Lactose intolerance is usually the result of lactase deficiency. If insufficient amounts of the enzyme lactase are available in the body (lactase deficiency), lactose passes in uncleaved form into the lower parts of the intestines (large intestine), where it is fermented by intestinal bacteria, causing, for example, gas to be produced and/or an increased inflow of water into the large intestine. This can lead to complaints such as stomach-ache, flatulence, bloating or diarrhoea, after the consumption of dairy products. This is referred to as lactose intolerance (milk sugar intolerance). Due to the similarity of the complaints, lactose intolerance is often confused with irritable bowel syndrome (irritable colon, spastic colon).

Three different forms of lactase deficiency are generally recognised:
1. Primary lactase deficiency
2. Secondary lactase deficiency
3. Congenital lactase deficiency The amount of lactase in the small intestine is highest in babies during the breast-feeding period and then declines continuously in most people for genetic reasons. The resulting so-called primary lactase deficiency is thus the result of a normal ageing process and can be observed in the vast majority (70%-90%) of the adult world population. Thus, almost all population groups in Africa and Asia do not tolerate lactose. But also in Germany, around 15% of adults have a primary lactase deficiency. The lactose intolerance resulting from primary lactase deficiency is then often referred to as primary lactose intolerance.

Various intestinal diseases can lead to a so-called secondary lactase deficiency (syn. acquired lactase deficiency), e.g. Crohn's disease, ulcerative colitis, coeliac disease (endemic sprue) and other intestinal inflammations (e.g. due to viral or bacterial infections). Also, after operations in the gastrointestinal tract, especially after removal of parts of the small intestine, secondary lactase deficiency is not uncommon. This is referred to as secondary or transitory lactose intolerance. Secondary lactase deficiency is usually reversible after the intestinal disease that caused it has been cured.

In the very rarely occurring congenital lactase deficiency, the newborn lacks the gene responsible for lactase production. This leads to an inability of the body to produce the enzyme at all. Strict lactose-free nutrition should be maintained in such babies.

In the sense of this patent application, the term lactase deficiency is used to mean not only the medically defined lactase deficiency, but any form of lactase deficiency.

Not all disturbances of lactose metabolism necessarily lead to severe lactose intolerance. However, complaints can also be observed in mild disturbances of lactose metabolism. Up to now, it has only been possible to avoid the above-mentioned complaints by keeping to a low-lactose or lactose-free diet or by taking preparations that contain the enzyme lactase when eating foods that contain lactose. Keeping to a low-lactose or lactose-free diet is unsatisfactory and, due to the valuable nutrients and vital substances contained in dairy products, also unfavourable from a nutritional physiological point of view. The choice of lactose-free dairy products is limited and, apart from this, they taste sweeter than lactose-containing dairy products, due to the lactose already being cleaved by the addition of lactase during production. Many consumers do not like the taste of these products. In addition, there are very many foods that one would not expect to contain lactose. This means that purchasing lactose-free foods often causes problems. The prompt use of lactase preparations represents a good alternative and often considerably improves the quality of life of those affected. The amount of individually required lactase depends, on the one hand, on the sensitivity of the user towards lactose. This is mainly determined by the residual activity of endogenous lactase. Apart from this, the amount of lactase required depends on the type of food, the total amount of food consumed and the amount of lactose it contains. It is known that lactase preparations are not always effective or equally effective in all of those affected.

A number of products have been proposed for use in treating or alleviating the symptoms of lactose intolerance or lactase deficiency.

RU 292125 discloses combinations of earth apple (Jerusalem artichoke) extract, a lactase and a fermented milk base containing *S. thermophilus* and *L. bulgaricus*. The product is intended for consumption by people suffering from lactose intolerance or lactase deficiency and the purpose of the lactase would appear to be in reducing the lactose content of the milk base. There is no suggestion that the two microorganisms have any beneficial effect on lactose intolerance. Furthermore, it is stated that the two microorganisms must be present in the ratio of *S. thermophilus*:*L. bulgaricus* 1:4 in order to provide the best taste and consistency.

DE2725731 (equivalent to U.S. Pat. No. 4,034,115) discloses a four stage process for preparing a fermented milk product which is low in lactose and is therefore suitable for consumption by people suffering from lactose intolerance. It is not intended to provide a general means of preventing or treating lactose intolerance or the symptoms of lactase deficiency that may arise from lactose in other types of foodstuff. The process comprises a first fermentation step using lactic acid bacteria (not *S. thermophilus* or *L. bulgaricus*) to give a buttermilk; a second fermentation step using yoghurt bacteria such as *S. thermophilus* or *L. bulgaricus*; a third step involving addition of a small amount of colostrum; and a fourth step involving fermentation with *L. acidophilus* or *L. bifidus*.

WO2009/056979 (Danisco) discloses inter alia dairy products (yoghurts) containing *S. thermophilus*, *L. bulgaricus* and exogenous lactase. The products are not intended to treat or prevent lactose intolerance or lactase deficiency although page 11 line 4 refers to the known use of lactase in treating lactose intolerance.

WO2004/089290 (Pharmachem) discloses the administration of chewable confections containing a combination of probiotic microorganisms and lactase to a lactose intolerant person. The list of preferred microorganisms includes *S. thermophilus* but not *L. bulgaricus*. The purpose of the lactase (see page 16) would appear to be to remove any lactose present in the confections. WO2004/089290 contains no examples of any confections containing lactase and/or a microorganism such as *S. thermophilus* or *L. bulgaricus* and there is no disclosure as to the form in which the microorganisms are presented. On pages 2 and 3 of WO2004/089290, it is suggested that the use of freeze dried microorganisms is problematic and elsewhere at numerous points it is stated that the confections are prepared without heating and dehydration, thereby suggesting that the microorganisms are not used in a dried form.

US2008/0187525 (Porubcan) discloses combinations of probiotic microorganisms and lactogenic enzymes. The lactogenic enzymes (which include lactase) are intended to promote growth of the probiotic microorganisms. The combinations (or their components) can be presented in capsule form. The microorganisms can be in freeze dried form. Specific combinations of lactase and either of *S. thermophilus* or *L. bulgaricus* are neither disclosed nor exemplified. This document is not concerned with the prophylaxis or treatment of lactose intolerance or lactase deficiency.

DE69505374 (=WO95/34292) discloses microgranules containing various bioactive substances such as lactase and microorganisms, where the microgranules are enterically coated. The coated microgranules are intended to be incorporated into foodstuffs such as milk products. *S. thermophilus* and *L. bulgaricus* are mentioned as examples of microorganisms. Lactose intolerance is discussed on page 3 and lactase is mentioned. There are examples of coated granules containing lactase and there are also examples of coated granules containing *L. acidophilus*. However, there are no disclosures of the use of lactase and *S. thermophilus* or *L. bulgaricus* in combination and there are no examples of coated granules containing either *S. thermophilus* or *L. bulgaricus*.

EP1112002 discloses milk powders for administration to animals. The milk powders contain lactase which is added to prevent symptoms of lactose intolerance in the animals. The powders may also contain probiotic microorganisms (see page 3). *S. thermophilus* is among the list of microorganisms but *L. bulgaricus* is not. However, there are no examples of milk powders containing probiotic microorganisms as well as the lactase.

WO96/06924 (=DE 69535290) discloses a process for producing a fermented product rich in galacto-oligosaccharides and β-galactosidase (lactase) by fermenting a medium containing *S. thermophilus*. On page 12, it is stated that the products are tolerated by persons suffering from lactase deficiency. There does not appear to be any disclosure of the addition of exogenous lactase and it does not appear to be suggested that the product could be used to prevent or treat lactose intolerance or lactase deficiency.

US2008/0213320 (Eisenstein Mayer) discloses compositions (which may be inter alia tablets or capsules) for treating gastro-oesophageal reflux disorders which contain at least two of (1) a digestive enzyme, (2) a probiotic, and (3) stevia. Lactase is among a list of digestive enzymes. *S. thermophilus* and *L. bulgaricus* are listed amongst the probiotics but are not stated to be preferred. One example is provided and this contains lactase as well as 7 other digestive enzymes but it also contains 6 probiotic species, which do not include *S. thermophilus* and *L. bulgaricus*. There is no reference to treating or preventing lactose intolerance or lactase deficiency.

US2009/110674 (Loizou Nicos) discloses health food supplements containing over fifty different active components selected from inter alia minerals, enzymes, vitamins, plant extracts, selected probiotics and amino acids. On page 3, a composition is described which contains over fifty ingredients including lactase (5 mg) and *Lactobacillus bulgaricus* (2.5 mg including *Bifidus*). On page 12, the lactase is described as being essential for hydrolysis of lactose in milk and it is stated that a deficiency of the enzyme causes lactose intolerance. The compositions are described as a universal panacea covering general health and are not aimed at any one disease state or condition.

US2008/0260708 is concerned with compositions for "normalising human body chemistry" and is intended as a universal panacea for promoting good health. The compositions must contain inter alia a digestive enzyme, soluble and insoluble fibre, a laxative, one or more probiotics, protease, lipase, various minerals and various herbal and plant extracts. The compositions are not specifically aimed at preventing or treating lactose intolerance or the symptoms of lactase deficiency. The digestive enzymes can include lactase and the pro-biotic enzymes can include *Lactobacillus bulgaricus* and *Streptococcus thermophilus*.

U.S. Pat. No. 6,008,027 (Langner) discloses capsules containing lactase-producing microorganisms for treating lactase deficiency. Although *L. bulgaricus* and *S. thermophilus* are mentioned, the exemplified compositions only contain *L. acidophilus*. There is no disclosure in U.S. Pat. No. 6,008,027 of the inclusion of exogenous lactase. An essential feature of the Langner capsules is that they are coated in an enteric polymer which prevents release in the acid conditions of the stomach but which breaks down to release the microorganisms in the intestines.

U.S. Pat. Nos. 6,410,018, 6,428,786, 6,562,338 and 6,562,339 (all to Eisenhardt et al) each disclose compositions for treating lactose intolerance that comprise a first lactase enzyme having an optimum working pH in the range from 3 to 6 and a second lactase enzyme having an optimum pH in the range from 6 to 8. The second lactase enzyme has an enteric coating in order to prevent premature degradation in the stomach. None of the documents suggest the use of lactic acid bacteria in the compositions, methods and processes described therein.

Guarner et al. *Brit. J. Nutrition,* 93 (2005), 783-786 disclose that the yoghurt bacteria *S. thermophilus* and *L. bulgaricus* have high lactase activity and that yoghurt improves lactose digestion and eliminates symptoms of lactose intolerance. However, there is no suggestion in Guarner et al. that exogenous lactase can be added or that any benefit would result from doing so.

Furthermore, no evidence is presented in Guarner et al. to indicate that consuming yoghurts containing *S. thermophilus* and *L. bulgaricus* would have any effect on lactose digestion in lactose malabsorbing subjects who have consumed other dairy products such as unfermented milk and ice cream.

Although the consumption of yoghurt may provide general benefits to some lactose malabsorbers who enjoy consuming yoghurt, many people do not like the taste and texture of yoghurt. Consequently, yoghurt containing live cultures of bacteria such as *S. thermophilus* and *L. bulgaricus* does not provide a general solution to the problem of lactose malabsorption and lactose intolerance.

Guarner et al (see above) emphasise the importance of using live cultures in order to produce any beneficial effects. If the yoghurt is heat-treated, the benefits are lost. Guarner et al. provide no evidence to suggest that administering dormant bacteria (e.g. freeze dried bacteria) in a non-dairy medium would provide any benefit to sufferers from lactose intolerance. According to the disclosure in WO2004/089290 (Pharmachem), which addresses the issue of lactose intolerance, the use of dehydrated bacteria is undesirable. For example, on page 2 of WO2004/089290, it is stated that "Lyophilized, i.e. freeze dried, probiotic organisms are also available. Freeze dried bacteria are in an abiotic state. The need to wet the microorganism before administration, in order to reinstate vitality, is a disadvantage since many bacteria will not survive rehydration. Moreover, the surviving organisms, if any, are not immediately metabolically active, and cannot survive the extreme, acidic conditions of the stomach". Thus, according to WO2004/089290, the use of dried bacteria does not offer a way forward.

Hove et al., *Amer. J. Clin. Nutr.,* 1994, 59: 74-79, describe experiments carried out on subjects suffering from lactose malabsorption in which the subjects were given capsules containing freeze dried mixed lactic acid bacteria containing *B. bifidum, L. acidophilus, S. thermophilus* and *L. bulgaricus*. Hove et al. concluded that the capsules containing the freeze dried lactic acid bacteria did not relieve the symptoms of Lactose malabsorption (i.e. abdominal cramps, diarrhoea and "meteorism") and did not enhance lactose hydrolysis in the small intestine in subjects with lactose malabsorption.

Therefore, in view of the disclosures discussed above, there remains a need for an effective product which enables lactose intolerant subjects to consume lactose-containing foodstuffs—other than yoghurts containing live bacteria which are better tolerated by some of the sufferers—without suffering from the symptoms usually associated with lactose intolerance.

Thus, an agent with a more reliable and/or better effect than that of preparations only containing the enzyme lactase would thus satisfy an existing urgent need for the many people affected and mean a considerable improvement and dramatic step forward in the nutritional options available in the case of lactose intolerance.

SUMMARY OF THE INVENTION

An object of the present invention is to provide a more effective agent for use in treating or preventing the symptoms of lactose intolerance and lactase deficiency, and to enable a subject to consume lactose-containing foods even if the subject suffers from lactose intolerance. Further, it is an object of the invention to make it possible for those affected by lactose intolerance to eat foodstuffs that they were not allowed to eat up to now, due to their lactose content. Moreover, the objective is to provide an agent that can prevent, reduce or eliminate the occurrence of lactose intolerance symptoms after the intake of lactose-containing foods or lactose-containing substances.

The present inventors have found that administration of the bacteria *Lactobacillus delbrueckii* ssp *bulgaricus* and *Streptococcus thermophilus* in dried form to subjects suffering from lactose malabsorption produced no statistically significant improvement in lactose digestion. This finding is consistent with the teachings in WO2004/089290 and Hove et al. discussed above.

However, the present inventors have also found that compositions containing combinations of lactase and *Lactobacillus delbrueckii* ssp *bulgaricus* and/or *Streptococcus thermophilus* in an uncoated dried form, when administered to subjects suffering from lactose malabsorption, are considerably more effective and reliable in improving lactose digestion, and exert their beneficial properties in a wider range of subjects, than compositions containing only the lactase.

Thus, contrary to what is suggested in the prior art discussed above, and in particular U.S. Pat. No. 6,008,027 (Langner) and WO2004/089290 (Pharmachem), a non-dairy composition containing a combination of lactase and the bacteria *Lactobacillus delbrueckii* ssp *bulgaricus* and/or *Streptococcus thermophilus* in an uncoated dried form can provide an effective means of improving lactose digestion in lactose malabsorbing subjects.

Thus, the present invention provides an effective agent for enabling people suffering from lactose intolerance to consume lactose-containing foodstuffs without suffering from the symptoms of lactose intolerance.

Accordingly, in a first embodiment (Embodiment 1.1), the invention provides a composition for use in therapy of lactose intolerance or conditions arising from lactase deficiency, wherein the composition is a non-dairy solid dosage form comprising:
(a) a lactase which is active in a pH range of 3 to 6; and
(b) one or more lactase-producing and/or lactase-containing microorganisms selected from *Lactobacillus delbrueckii* ssp *bulgaricus* and *Streptococcus thermophilus;*
wherein the lactase (a) is other than a lactase derived from the said one or more microorganisms (b); and wherein the one or more lactase-producing and/or lactase-containing microorganisms (b) are in dried form.

In further embodiments, the invention provides:
1.2 A composition for use according to Embodiment 1.1 wherein the dosage form is other than a capsule coated with an enteric coating.
1.3 A composition for use according to Embodiment 1.1 wherein the lactase-producing and/or lactase-containing organisms are not enterically coated.
1.4 A composition for use according to any one of Embodiments 1.1 to 1.3 wherein the lactase (a) is one which still has at least 30% of its activity after one hour at 37° C. at a pH in the range from 2 to 6.
1.5 A composition for use according to any one of Embodiments 1.1 to 1.3 wherein the lactase (a) is one which still has at least 30% of its activity after one hour at 37° C. at a pH in the range from 3 to 6.

1.6 A composition for use according to any one of Embodiments 1.1 to 1.3 wherein the lactase (a) is one which still has at least 30% of its activity after one hour at 37° C. at a pH in the range from 4 to 6.

1.7 A composition for use according to any one of Embodiments 1.1 to 1.3 wherein the lactase (a) exhibits peak activity at a pH in the range from 3 to 6.

1.8 A composition for use according to any one of Embodiments 1.1 to 1.3 wherein the lactase (a) exhibits peak activity at a pH in the range from 4 to 6.

1.9 A composition for use according to any one of Embodiments 1.1 to 1.8 wherein the lactase (a) is derived from a microorganism, and the composition is substantially free of the microorganism from which the lactase is derived.

1.10 A composition for use according to any one of Embodiments 1.1 to 1.9 which contains both *Lactobacillus delbrueckii* ssp *bulgaricus* and *Streptococcus thermophilus*.

1.11 A composition for use according to any one of Embodiments 1.1 to 1.10 wherein the solid dosage form is selected from capsules, tablets, dragees, powders, pellets and granules.

1.12 A composition for use according to any one of Embodiments 1.1 to 1.11 which is in unit dosage form.

1.13 A composition for use according to Embodiment 1.12 wherein the unit dosage form is selected from capsules, tablets, dragees and sachets containing a powder, pellets or granules.

1.14 A composition for use according to Embodiment 1.13 wherein the unit dosage form is a capsule.

1.15 A composition for use according to any one of Embodiments 1.1 to 1.14 which contains between 2000 and 12000 FCC-units of the lactase (a).

1.16 A composition for use according to Embodiment 1.15 which contains between 2000 and 6000 FCC-units of the lactase (a).

1.17 A composition for use according to any one of Embodiments 1.1 to 1.16 which contains between from 50 million to 10 billion colony forming units of *Lactobacillus bulgaricus* and from 50 million to 10 billion colony forming units of *Streptococcus thermophilus*.

1.18 A composition for use according to Embodiment 1.17 which contains from 100 million to 2 billion colony forming units of *Lactobacillus bulgaricus* and from 100 million to 2 billion colony forming units of *Streptococcus thermophilus*.

1.19 A composition for use according to any one of Embodiments 1.1 to 1.18 which is substantially free of lactose.

1.20 A composition for use according to any one of Embodiments 1.1 to 1.19 wherein the *Lactobacillus bulgaricus* is *Lactobacillus delbrueckii* LB-VC18 (deposition number: DSM 23320).

1.21 A composition for use according to any one of Embodiments 1.1 to 1.20 wherein the *Streptococcus thermophilus* is *Streptococcus thermophilus* ST-VC18 (deposition number: DSM 23319).

1.22 A composition for use according to any one of Embodiments 1.1 to 1.21 wherein the lactase (a) is derived from an *Aspergillus* species.

1.23 A composition for use according to Embodiment 1.22 wherein the lactase (a) is derived from *Aspergillus oryzae* or *Aspergillus niger*.

1.24 A composition according to Embodiment 1.23 wherein the lactase (a) is derived from *Aspergillus oryzae*.

1.25 A composition for use according to any one of Embodiments 1.1 to 1.24 wherein the composition is other than a composition containing in combination two or more added herbal extracts together with exogenous lipase and exogenous protease.

1.26 A composition for use according to any one of Embodiments 1.1 to 1.25 wherein the composition contains (c) a pharmaceutically or dietarily acceptable carrier or excipient.

1.27 The use of a combination of:
(a) a lactase which is active in a pH range of 3 to 6;
(b) one or more lactase-producing and/or lactase-containing microorganisms selected from *Lactobacillus delbrueckii* ssp *bulgaricus* and *Streptococcus thermophilus*;
wherein the lactase (a) is other than a lactase derived from the said one or more microorganisms (b); and wherein the one or more lactase-producing and/or lactase-containing microorganisms (b) are in dried form; and
wherein the lactase (a) and lactase-producing and/or lactase-containing microorganisms (b) are as defined in any one of Embodiments 1.1 to 1.26;
for the manufacture of a non-dairy solid dosage form composition for use in therapy of lactose intolerance or conditions arising from lactase deficiency.

1.28 A method for the therapy of lactose intolerance or conditions arising from lactase deficiency, which method comprises administering to a subject in need thereof an effective amount of a composition as defined in any one of Embodiments 1.1 to 1.26.

1.29 A solid dosage form selected from capsules, tablets, dragees, powders, pellets and granules which is not coated by an enteric coating and which contains a lactase and one or more lactase-producing and/or lactase-containing microorganisms selected from *Lactobacillus delbrueckii* ssp *bulgaricus* and *Streptococcus thermophilus* as defined in any one of Embodiments 1.1 to 1.26; provided that the composition is other than a composition containing in combination two or more added herbal extracts together with exogenous lipase and exogenous protease.

1.30 A solid dosage form according to Embodiment 1.29 which is selected from capsules, tablets and dragees.

1.31 A solid dosage form according to Embodiment 1.29 which is selected from powders, pellets and granules and wherein the said powders, pellets and granules are contained in a sachet.

1.32 A solid dosage form according to Embodiment 1.30 which is a capsule.

1.33 A solid dosage form according to Embodiment 1.30 which is a tablet.

1.34 A solid dosage form according to Embodiment 1.30 which is a dragee.

Further Aspects and Embodiments of the Invention

Further embodiments and aspects of the invention will be apparent from the following description and the examples.

The subject matter of the invention is an agent that can solve the problems described above in the introductory section of this application. The agent contains the enzyme lactase in combination with microorganisms. The microorganisms in question are lactic acid bacteria and particularly preferably *Lactobacillus delbrueckii* subspecies *bulgaricus* and/or *Streptococcus thermophilus*. A lactase in the sense of this invention is an enzyme that is capable of converting (cleaving) lactose into glucose and galactose. Lactic acid bacteria in the sense of this invention are in particular microorganisms that, by means of their own microbial lactase, can metabolise lactose and/or from which lactase can be released in the digestive tract of humans or animals. The microorganisms to be used according to the present invention can preferably be freeze dried or spray dried (preferably freeze dried), in order to provide a longer shelf-life and good processability.

Whenever *Lactobacillus bulgaricus* is used below, this refers to *Lactobacillus delbrueckii* subspecies (subsp.) *bulgaricus*.

The agent according to the present invention can cause lactose in the food or in the food pulp to be cleaved into glucose and galactose after consumption. This means that the lactose is no longer available for the bacterial metabolism characterised by fermentation in the intestines.

The subject matter of the invention is therefore an agent that, with the aid of lactase in combination with microorganisms, preferably lactic acid bacteria, particularly preferably *Lactobacillus bulgaricus* and/or *Streptococcus thermophilus*, reduces the bioavailability of lactose in the human or animal body.

The subject matter of the invention is also an agent that, with the aid of lactase in combination with microorganisms, preferably lactic acid bacteria, particularly preferably *Lactobacillus bulgaricus* and/or *Streptococcus thermophilus*, reduces the amount of lactose available for the human or animal body or for intestinal bacteria colonised therein.

The subject matter of the invention is further an agent for use in the case of lactose intolerance that contains lactase in combination with microorganisms, preferably lactic acid bacteria, particularly preferably *Lactobacillus bulgaricus* and/or *Streptococcus thermophilus*.

A further subject matter of the invention is the use of lactase in combination with microorganisms, preferably lactic acid bacteria, particularly preferably *Lactobacillus bulgaricus* and/or *Streptococcus thermophilus*, in the case of lactose intolerance.

Lactase is an enzyme that has the property of converting lactose into glucose and galactose. While lactose is not absorbed from the small intestine, glucose and galactose are monosaccharides that are easily digestible and are rapidly absorbed. The lactases currently used in lactase preparations intended for oral use are so-called acid lactases (sometimes referred to as sour lactases) that are mostly produced using *Aspergillus oryzae*. Acid lactase is very effective in the acidic milieu of the stomach after consumption of food. Acid lactase is stable and active at a pH of around 3-6. In the sense of this application, the term "stable" means that the acid lactase still has at least 30% of its activity after one hour at 37° C. and pH values of 3-6. The reference to 30% of its activity in the present context refers to the residual activity of the enzyme if, after the one hour period specified, it is tested according to the assay for acid lactase as described in the sixth edition of the Food Chemical Codex (FCC).

At a pH value of over 6.5, as is found in the small intestine, acid lactase is stable but no longer very active. Therefore, acid lactase can no longer develop a satisfactory effect in the small intestine. At present, lactase preparations therefore have to contain as much lactase as is necessary to cleave the amounts of lactose usually consumed with food as far as possible in the stomach. A lactase that is stable and active at low pH values and that is effective both in the acidic milieu of the stomach and in the small intestine is not known and is not commercially available. Since the gastric transit time varies greatly depending on the food consumed and the amount of food consumed, the correct dosage of lactase preparations is often a problem for the user and consequently, as described above, users are often dissatisfied with the effect of these products. An increase in the lactase activity per dose unit can be helpful, but it has been found that the increase in effect and the reliability of the effect do not increase proportionally to the lactase activity per dose unit. The time of intake is also critical, since acid lactase is rapidly inactivated at the very low pH value (between 1 and 2.5) prevailing in the empty stomach. Thus, if a user consumes a lactase preparation too long (e.g. 10 minutes) before a meal on an empty stomach, it is possible that the enzyme has already irreversibly lost its activity at the time of food intake and is then no longer available for the desired lactose cleavage, so that in this case the lactase activity per dose unit does not play a role.

Certain lactic acid bacteria contain a lactase that is active and stable at the pH values prevailing in the small intestine. The lactic acid bacteria-lactase, protected by the bacterial shell, can at least partially (or to a certain extent) pass through the stomach into the small intestine, where two advantageous effects can come into play. On the one hand, the microbial lactase can be released when the bacterial shell is destroyed by the digestive juices in the small intestine, so that lactose that has not yet been cleaved in the stomach by acid lactase is then cleaved by this lactase released by the lactic acid bacteria. On the other hand, bacteria that remain intact can metabolise lactose and thus also contribute to a further reduction of the amount of lactose in the small intestine. Some people affected by lactose intolerance have a better tolerability of fermented dairy products as opposed to unfermented dairy products, which is in part due to the lactase content of lactic acid bacteria. However, most of those affected cannot consume fermented dairy products without problems either. In studies in which people intolerant to lactose were administered lactic acid bacteria, it was shown that they do not have a good and reliable efficacy in relation to lactose digestion. This result has been shown for a large number of different strains, also when used in a wide range of different combinations. The use of a preparation in the case of lactose intolerance, that exclusively contains lactic acid bacteria, does not therefore make sense (see e.g. Hove et. al as mentioned above). Whereas today the attempt is often made to add lactic acid bacteria to dairy products and other foods, that reach the large intestine intact in order to exert advantageous effects on health there, in the invention presented here it is preferred that as many as possible of the lactic acid bacteria consumed are destroyed in the small intestine, so that their microbial lactase is released there, so that it is then available for lactose cleavage. By adding such lactic acid bacteria, the efficacy and/or reliability of lactase preparations can be increased. Such a preparation is capable, on the one hand, of cleaving lactose in the stomach (through the acid lactase) and, on the other, of cleaving the lactose that was not cleaved in the stomach in the small intestine (by means of the lactic acid bacteria-lactase). Thus, by adding lactic acid bacteria, a prolonged effect of the preparation is achieved, which leads to a greater efficacy and/or reliability of effect, which cannot be achieved by purely increasing the lactase activity per dose unit or at least cannot be achieved so cost-effectively. In addition to the enzyme lactase, it is thus advantageous to add such microorganisms to the agent according to the present invention, that release their own sufficiently active and stable lactase in the small intestine and/or metabolise lactose in the small intestine. It has been found that the lactic acid bacteria *Lactobacillus bulgaricus* and *Streptococcus thermophilus* are particularly well suited for this application, since these microorganisms predominantly, but at least partially, survive the stomach with an intact bacterial shell protecting the microbial lactase, but predominantly, but at least partially, do not survive the small intestine intact and thus release their microbial lactase there to a relevant extent. The following also come into question, for example: *Lactobacillus delbrueckii* (subsp. other than *Lactobacillus bulgaricus*), *Lactobacillus acidophilus*, *Lactobacillus rhamnosus*, *Lactobacillus casei*, *Lactobacillus*

*paracasei, Lactobacillus brevis, Lactobacillus plantarum, Lactobacillus salivarius, Lactobacillus rheuteri, Lactococcus lactis, Pediococcus acidilacti, Bifidobacterium lactis, Bifidobacterium bifidum, Bifidobacterium breve, Bifidobacterium longum, Bifidobacterium infantis.*

Such a combined agent can be applied in the form of two separate dose units, e.g. in two separate tablets or capsules, of which the one contains the enzyme lactase and the other the lactic acid bacteria.

Foodstuffs in the sense of this invention are foodstuffs in the sense of Regulation (EC) No. 178/2002 of the European Parliament and of the Council of 28 Jan. 2002. The foodstuffs in the sense of this invention include in particular foodstuffs for particular nutritional uses, foods for special medical purposes, food supplements, dietary supplements and food additives.

Food supplements in the sense of this invention are food supplements in the sense of Directive 2002/46/EC of the European Parliament and of the Council of 10 Jun. 2002.

Foodstuffs for particular nutritional uses in the sense of this invention are foodstuffs for particular nutritional uses in the sense of Directive 2009/39/EC of the European Parliament and of the Council of 6 May 2009 on foodstuffs intended for particular nutritional uses.

Foods for special medical purposes in the sense of this invention are foods for special medical purposes in the sense of Directive 1999/21/EC of the Commission of 25 Mar. 1999 on dietary foods for special medical purposes.

This invention provides the enzyme lactase in combination with lactic acid bacteria, in particular in combination with *Lactobacillus bulgaricus* and/or *Streptococcus thermophilus* for use in medicine, for example as a pharmaceutical composition. The subject matter of the invention is accordingly also a product that consists of lactase in combination with *Lactobacillus bulgaricus* and/or *Streptococcus thermophilus* or contains these substances alongside one or more other active ingredients, for use in a medical procedure, in particular a procedure for therapeutic treatment of the human or animal body.

The subject matter of the invention is also a composition for use in medicine, containing a lactase and one or more lactase-producing and/or lactase-containing microorganisms, selected from *Lactobacillus bulgaricus, Lactobacillus delbrueckii, Lactobacillus acidophilus, Lactobacillus rhamnosus, Lactobacillus casei, Lactobacillus paracasei, Lactobacillus brevis, Lactobacillus plantarum, Lactobacillus salivarius, Lactobacillus rheuteri, Lactobacillus lactis, Pediococcus acidilacti, Bifidobacterium lactis, Bifidobacterium bifidum, Bifidobacterium breve, Bifidobacterium longum, Bifidobacterium infantis* and *Streptococcus thermophilus*, whereby the lactase preferably does not originate from the aforementioned microorganism(s). In the sense of this invention, a pharmaceutical composition is a product in the sense of the Directive 2001/83 EC in the version of the Directive 2004/27 EC.

According to a further aspect of the present invention, a foodstuff is provided that contains lactase in combination with lactic acid bacteria, in particular in combination with *Lactobacillus bulgaricus* and/or *Streptococcus thermophilus*. Further, according to the present invention, a foodstuff is provided that contains lactase in combination with lactic acid bacteria, in particular in combination with *Lactobacillus bulgaricus* and/or *Streptococcus thermophilus*, in an amount effective for converting lactose to glucose and galactose.

A foodstuff can also be produced using a procedure in which lactase in combination with *Lactobacillus bulgaricus* and/or *Streptococcus thermophilus* is added to the foodstuff in such a way in which the effect of the lactase and the lactic acid bacteria predominantly starts after consumption of the foodstuff. Such a foodstuff tastes virtually the same as an untreated foodstuff and, as a result of the reduced lactose content occurring after consumption, is suitable for consumption in the case of lactose intolerance. Predominantly in the sense of this application means that at least 50% of the lactose-cleaving effect of the enzyme and of the lactic acid bacteria occurs after consumption of the foodstuff. Alternatively, (a) at least 90%, (b) at least 80%, (c) at least 70% or (d) at least 60% of the effect can occur after consumption of the foodstuff.

According to a further aspect of the present invention, a medical device is provided that contains lactase in combination with lactic acid bacteria, in particular in combination with *Lactobacillus bulgaricus* and/or *Streptococcus thermophilus*. The subject matter of the invention is accordingly also a medical device that contains lactase in combination with lactic acid bacteria, in particular in combination with *Lactobacillus bulgaricus* and/or *Streptococcus thermophilus*, or contains it alongside one or more other active ingredients.

A medical device in the sense of this patent application is a medical device in the sense of Directive 93/42/EEC in the version amended by Directive 2007/47/EC.

The various aspects of the invention are further described below. Insofar as an agent is referred to below, this always also means a foodstuff, medical device or pharmaceutical composition.

Lactase, specifically acid lactase, more specifically acid lactase derived from *Aspergillus* spp, even more specifically acid lactase derived from *Aspergillus oryzae*, has not yet been used in combination with *Lactobacillus bulgaricus* and/or *Streptococcus thermophilus* in the medical-pharmaceutical field, in particular in the case of lactose intolerance in humans or animals. Consequently, the invention presented here is the first medical indication for the combination of these substances.

The agents according to the present invention can be taken orally before meals, with meals or after meals, so that they can exert their cleaving effect on the lactose in the food pulp. Preferably, the agents according to the present invention are taken just before meals, during meals or immediately after meals. The agents according to the present invention may contain the enzyme and the lactic acid bacteria without further additives. However, it is preferable that the agents according to the present invention further contain additives that are pharmaceutically acceptable and/or acceptable for foodstuffs, such as extenders, binders, stabilizers, preservatives, flavourings, etc. Such additives are commonly used and well known for the production of pharmaceutical compositions, medical devices, foodstuffs, foodstuffs for particular nutritional uses, foods for special medical purposes, food supplements, dietary supplements and food additives, and the specialist in this field knows which additives in which amounts are suitable for particular presentation forms. Particularly preferably, the agents according to the present invention contain as additives dicalcium phosphate, modified starch, microcrystalline cellulose, maltodextrin and/or fibersol.

The agents according to the present invention can also be added to a foodstuff before consumption. They can even be added to the foodstuff at the production stage, with the aim of developing their effect at least partially but preferably predominantly after consuming the foodstuff. This could be achieved by microencapsulation, for example. In this way, the useable lactose content of the foodstuff would be reduced in a particularly advantageous way. Therefore, preparations containing lactase in combination with *Lactobacillus bulgaricus* and/or *Streptococcus thermophilus* are preferred that predominantly do not release these substances until they enter the digestive tract of a human or animal especially in the stomach or small intestine. Therefore, the invention could be used for example in the production of milk and dairy products, such as curd, yoghurt, cream, cheese, pudding, milk beverages, milk mixed beverages and ice-cream, and in the production of, e.g. chocolate and chocolate products, bakery products (e.g. biscuits and cakes), breads, sweets, lactose containing beverages, lactose containing sauces (e.g. cream sauces) and lactose containing sweeteners. For dishes that are boiled, baked or fried, the agents according to the present invention could, e.g. be mixed into or sprinkled onto them after cooling. As far as milk and dairy products are concerned, according to the present invention they contain acid lactase and at least one of the microorganisms listed in this application, preferably *Lactobacillus bulgaricus* and *Streptococcus thermophilus*, but not *Lactobacillus acidophilus*.

The agents according to the present invention can also be added to a foodstuff in order to exert its effect after consumption on the lactose originating from another foodstuff. An example of this would be the addition of the agents according to the present invention to cereals, so that the reduction of the lactose contained in the milk occurs after consumption of the cereals prepared with the milk, without impairing the taste of the milk.

A subject matter of the invention are also agents that in addition to other active ingredients also contain lactase in combination with *Lactobacillus bulgaricus* and/or *Streptococcus thermophilus*.

The invention may be formulated in any form which is suitable for the intended route of administration. For oral administration, the agents according to the present invention are preferably formulated in the form of capsules (coated or non-coated), tablets (coated or non-coated), dragees (coated or non-coated), capsules containing coated or non-coated pellets, granules, or micro- or mini-tablets, tablets pressed from coated or non-coated powder, pellets or micro- or minitablets. Possible for oral administration are also coated or non-coated gel caps (soft gelatin capsules), or liquid forms, e.g. a solution, drops, a suspension or a gel. The invention can also be presented as a dry or moist oral supplement. The formulation of the agents according to the present invention as a powder is particularly suitable for an admixture to a foodstuff. The powder may be sprinkled onto a meal or it may be mixed into a pulp or a beverage. It is particularly suitable if the agent offered as bulk powder is packed in single dosage amounts, such as in single bags, or if it is provided in a dosing apparatus.

It is especially preferable if the agent according to the present invention is formulated as a powder or as granules or pellets in capsules or as a tablet that are administered orally.

The agents or compositions of the invention typically contain at least one pharmaceutically or dietarily acceptable carrier or excipient.

For oral administration, the active ingredients may be contained in acceptable excipients and/or carriers. The term "acceptable carrier" relates to a carrier that delivers the active ingredient to its target site and which does not cause significant harm to the recipient, human or animal. However, the exact form of the carrier is not important.

A carrier may be, for example, a capsule shell, a sachet or a matrix within which the active ingredients are encased.

The total amount of the carrier and/or excipient in relation to an agent according to the present invention is preferably between 5 and 99.9% by weight, more preferably between 10 and 95% by weight and even more preferably between 25 and 90% by weight of the composition.

Suitable excipients and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethyl cellulose, corn starch, modified starch, fibersol, gelatine, hydroxypropylmethyl cellulose and the like (including mixtures thereof). Preferable carriers include calcium carbonate, magnesium stearate, maltodextrin, dicalcium phosphate, modified starch, microcrystalline cellulose, fibersol, gelatine, hydroxypropylmethyl cellulose and mixtures thereof. The various ingredients and the excipient and/or carrier are mixed and formed into the desired form using common methods. The presentation form which is intended for oral administration according to the present invention, such as a tablet or capsule, may be coated with a coating that is resistant to low pH values or a gastro-resistant coating. Also a coating may be used which is not resistant against low pH values but which provides delayed release of the respective enzyme or of the respective lactic acid bacterium at low pH values. It is also possible to prepare the agent according to the present invention as coated (see above) pellets, granules, or micro- or mini-tablets which can be filled into non-coated capsules or which can be pressed into non-coated tablets. Suitable coatings are, for example, cellulose acetate phthalate, cellulose derivatives, shellac, polyvinylpyrrolidone derivatives, acrylic acid, polyacrylic acid derivatives and polymethyl methacrylate (PMMA), such as Eudragit (from Röhm GmbH, Darmstadt), in particular Eudragit FS30D and Eudragit L30D-55. By adding, for example, sodium hydroxide solution to the coating agent, the Ph resistance of this coating agent can be additionally influenced. Further details about formulation and administration methods can be found in the 21$^{st}$ edition of "Remington: The Science & Practice of Pharmacy", published in 2005 by Lippincott, Williams & Wilkins, Baltimore, USA and in Prof. Bauer "Lehrbuch der Pharmazeutischen Technologie", 18$^{th}$ edition, published in 2006 by Wissenschaftliche Verlagsgesellschaft (ISBN 3804-72222-9), whereby the documents are hereby incorporated by reference.

Although according to the present invention such lactic acid bacteria are preferably used that survive the stomach with their bacterial shell as far as possible intact, it may nevertheless be advantageous to apply a gastro-resistant coating to the lactic acid bacteria or to formulate them, e.g. in capsules, dragees, tablets, pellets, granules or crystals with a gastro-resistant coating, so that as large a proportion of the bacteria as possible reaches the small intestine or at least the duodenum (the upper part of the small intestine). The lactic acid bacteria could also be contained in, e.g. pellets, granules with a gastro-resistant coating, or a gastro-resistant coating could be applied to the lactic acid bacteria powder (e.g. using a spraying procedure). The pellets, granules or the powder could be filled into uncoated capsules. These could also contain the lactase that is supposed to be released in the stomach. A coating for protecting the lactic acid bacteria against gastric acid would be very advantageous in particular if lactic acid bacteria are used whose bacterial shell would otherwise be destroyed in the stomach, so that their microbial lactase would be inactivated in the stomach due to e.g. the low pH value there.

Other suitable pharmaceutically and/or dietarily acceptable carriers or excipients for use in the present invention include water, mineral oil, ethylene glycol, propylene glycol, lanolin, glyceryl stearate, sorbitan stearate, isopropyl myristate, isopropyl palmitate, acetone, glycerine, phosphatidylcholine, sodium cholate or ethanol, but are not limited thereto.

The compositions for use in the present invention may also comprise at least one coemulsifying agent, which includes oxyethylenated sorbitan monostearate, fatty alcohols, such as stearyl alcohol or cetyl alcohol, or esters of fatty acids and polyols, such as glyceryl stearate, but is not limited thereto.

Preferably, the agents to be used in the present invention are provided in a stabilized form. Generally, stabilization methods and procedures which may be used according to the present invention include any and all methods for the stabilization of chemical or biological material which are known in the art, comprising e.g. the addition of chemical agents, methods which are based on temperature modulation; methods which are based on irradiation or combinations thereof. Chemical agents that may be used according to the present invention include, among others, preservatives, acids, bases, salts, antioxidants, viscosity enhancers, emulsifying agents, gelatinisers, and mixtures thereof.

Acid lactase is commercially available (e.g. Amano Japan and DSM Netherlands) and is conventionally prepared in a microbiological way with the help of the microorganism *Aspergillus oryzae*. *Lactobacillus bulgaricus* and *Streptococcus thermophilus* are also commercially available (e.g. Danisco, Denmark, or Christian Hansen, Denmark). However, the invention is not limited to the acid lactase enzymes that are commercially available at the moment, but generally relates to enzymes that can bring about the conversion of lactose—specifically or unspecifically—to glucose and galactose in combination with lactic acid bacteria that can break down lactose in the small intestine, i.e. either by releasing lactase or through intracellular metabolisation of lactose.

The activity of lactase is defined according to the present invention in FCC units (Food Chemical Codex units). One enzyme unit releases one micromole o-nitrophenol per minute at 37° C. and Ph 4.5, under the conditions described in the sixth edition of the Food Chemical Codex (see complete measuring specification, test description, activity calculation there).

At an enzyme activity determined according to this definition, the agent according to the present invention should contain 500 to 50,000 FCC units, preferably 2000 to 20,000 FCC units and particularly preferably 3000 to 12,000 FCC units per dose unit of lactase.

If amounts are stated below (in colony forming units, abbreviated as cfu) with regard to the lactic acid bacteria contained in the agent according to the present invention, they refer to the amount of still viable lactic acid bacteria (in cfu) at the end of the shelf-life of the agent according to the present invention. It is to be noted that preparations containing lactic acid bacteria are preferably to be stored in a dry and cool place. Thus, in order to achieve a sufficiently long viability of the lactic acid bacteria, it can be advantageous to store the agent according to the present invention in an airtight and preferably water-vapour-impermeable container (e.g. made of glass or aluminium), equipped with a desiccant (e.g. in the lid), e.g. silica gel or molecular sieves.

The amount of lactic acid bacteria is stated in cfu (colony forming units). The agent according to the present invention should contain between 10 million and 200 billion (billion=thousand million) cfu, preferably between 50 million and 10 billion cfu and particularly preferably between 100 million and 2 billion cfu (e.g. between 100 million and 1 billion cfu) per lactic acid bacteria strain.

In the case of a combined agent that contains *Lactobacillus bulgaricus* and/or *Streptococcus thermophilus* in addition to the enzyme lactase, one dose unit should contain between 10 million and 200 billion cfu *Lactobacillus bulgaricus*, preferably between 50 million and 10 billion cfu *Lactobacillus bulgaricus* and particularly preferably between 100 million and 2 billion cfu (e.g. between 500 million and 2 billion cfu) *Lactobacillus bulgaricus*. In addition to or instead of the *Lactobacillus bulgaricus* bacteria, the agent according to the present invention should contain between 10 million and 200 billion cfu *Streptococcus thermophilus*, preferably between 50 million and 10 billion cfu *Streptococcus thermophilus* and particularly preferably between 100 million and 2 billion cfu (e.g. between 500 million and 2 billion cfu) *Streptococcus thermophilus* per dose unit.

An agent according to the present invention has proven to be particularly advantageous, which contains between 2000 and 12000 FCC units (e.g. between 2000 and 6000 FCC units) acid lactase, between 100 million and 10 billion cfu (e.g. between 100 million and 2 billion cfu) *Lactobacillus bulgaricus* and between 100 million and 10 billion cfu (e.g. between 100 million and 2 billioin cfu) *Streptococcus thermophilus* per dose unit. Particularly advantageous results can be achieved if the acid lactase is combined with the two strains *Lactobacillus delbrueckii* LB-VC18 (deposition number: DSM 23320) and *Streptococcus thermophilus* ST-VC18 (deposition number: DSM 23319) both deposited with the Deutsche Sammlung von Mikroorganismen and Zellkulturen GmbH (German Collection of Microorganisms and Cell Cultures) having an address at Inhoffenstraße 7B, 38124 Braunschweig, Germany on Feb. 11, 2010.

The wide range of the above mentioned dosages may be explained by the fact that the agent according to the present invention can be applied in a wide range of different severities and also in milder lactose metabolism disorders. The humans and/or animals affected react to a different degree to a certain lactose load. Apart from this, the different dosages also result from the fact that strongly varying amounts of lactose are supplied to the body, depending on the respective food consumed.

The agent according to the present invention may contain, for example between 500 and 50,000 FCC units (e.g. between 500 and 30,000 FCC units) lactase and between 10 million cfu and 200 billion cfu *Lactobacillus bulgaricus* and/or between 10 million cfu and 200 billion cfu *Streptococcus thermophilus* per dose unit. Instead of these two microorganisms or in addition to one or both of these microorganisms, the agent according to the present invention may in each case also contain between 10 million cfu and 200 billion cfu of the following lactic acid bacteria: *Lactobacillus delbrueckii* (subsp. other than *Lactobacillus bulgaricus*), *Lactobacillus acidophilus*, *Lactobacillus rhamnosus*, *Lactobacillus casei*, *Lactobacillus paracasei*, *Lactobacillus brevis*, *Lactobacillus plantarum*, *Lactobacillus salivarius*, *Lactobacillus rheuteri*, *Lactococcus lactis*, *Pediococcus acidilacti*, *Bifidobacterium lactis*, *Bifidobacterium bifidum*, *Bifidobacterium breve*, *Bifidobacterium longum*, *Bifidobacterium infantis*.

Apart from this, suitable additives may be used in the required amounts.

The invention can be made available for medical purposes and non-medical purposes, e.g. as a pharmaceutical composition, medical device or foodstuff.

The term therapy in the present context is to be understood in a broad sense. In the sense of this application, therapy not only refers to giving therapy for or treating diseases, but also includes very generally the use of the agent according to the present invention or of the agents according to the present invention in lactose intolerance and lactase deficiency in humans or in animals (since in almost all mammals the ability to digest lactose declines after breast-feeding is stopped). In the sense of this application, therapy accordingly encompasses in particular the use of the agent according to the present invention or of the agents according to the present invention to prevent, to eliminate, to alleviate, to reduce or to act as a preventive measure against the occurrence of (a) all types and severities of symptoms, (b) all types and severities of indispositions and (c) all forms of impairments to health and complaints that can occur as a result of the ingestion of lactose or lactose-containing foodstuffs or through the release of lactose in the digestive tract of humans or animals from other substances, e.g. pharmaceutical compositions. Further, in the sense of this application, therapy encompasses the elimination, alleviation, removal, the reduction, preventive measures against and the prevention of bloating, wind, stomach-ache, colicky stomach-ache, colic, diarrhoea, watery diarrhoea, bowel sounds, abdominal cramps, belching, nausea, vomiting, flatulence, microbiological imbalance in the intestines or increased production of intestinal gas associated with the ingestion of lactose or lactose-containing foodstuffs or with the release of lactose in the digestive tract of humans or animals from other substances, e.g. pharmaceutical compositions. Further, in the sense of this application, therapy encompasses the elimination, alleviation, removal, the reduction, preventive measures against and the prevention of any kind of depression, headaches, migraines, eczema, rashes and, lack of appetite and weight loss associated with the ingestion of lactose or lactose-containing foodstuffs or with the release of lactose in the digestive tract of humans or animals from other substances, e.g. pharmaceutical compositions or associated with insufficient lactose digestion or lactose malabsorption. Further, therapy in the sense of this invention encompass the reduction of the bioavailability of lactose in the human or animal body and the reduction of the amount of lactose available for the human or animal body or for the intestinal bacteria colonising therein.

In the context of this application the term therapy includes prophylaxis and treatment.

EXAMPLES

The invention will now be illustrated, but not limited, by reference to the examples set out below.

Example 1

Capsule Compositions

The following capsule compositions may be prepared by mixing lactase from *Aspergillus oryzae*, and lyophilised *Lactobacillus bulgaricus* and *Streptococcus thermophilus*.

Capsule Composition A—Size 1 Capsule

A size 1 gelatine capsule (volume 0.5 ml) obtainable from Capsugel BVBA, Bornem, Belgium is filled with 70 mg lactase (activity of the lactase is 50,000 FCC/g), 40 mg of lyophilised *Streptococcus thermophilus* (30 billion cfu/g), 30 mg of lyophilised *Lactobacillus bulgaricus* (50 billion cfu/g) and 200 mg dicalcium phosphate per capsule.

A preferred strain of *Streptococcus thermophilus* is *Streptococcus thermophilus* ST-VC18 (deposition number: DSM 23319) and a preferred strain of *Lactobacillus bulgaricus* is *Lactobacillus delbrueckii* LB-VC18 (deposition number: DSM 23320).

Capsule Composition A—Size 1 Capsule

A size 3 gelatine capsule (volume 0.3 ml) obtainable from Capsugel BVBA, Bornem, Belgium is filled with 70 mg lactase (activity of the lactase 50,000 FCC/g), 30 mg *Streptococcus thermophilus* (30 billion cfu/g), 20 mg *Lactobacillus bulgaricus* (50 billion cfu/g) and 100 mg dicalcium phosphate per capsule.

Capsule Composition C—Size 0 Capsule

A size 2 gelatine capsule (volume 0.68 ml) obtainable from Capsugel BVBA, Bornem, Belgium is filled with 150 mg lactase (activity of the lactase 50,000 FCC/g), 100 mg *Streptococcus thermophilus* (30 billion cfu/g), 50 mg *Lactobacillus bulgaricus* (50 billion cfu/g) and 250 mg dicalcium phosphate.

Capsule Composition D—Size 2 Capsule

A size 3 gelatine capsule (volume 0.37 ml) obtainable from Capsugel BVBA, Bornem, Belgium is filled with 100 mg lactase (activity of the lactase 100,000 FCC/g), 50 mg *Streptococcus thermophilus* (30 billion cfu/g), 30 mg *Lactobacillus bulgaricus* (50 billion cfu/g) and 100 mg dicalcium phosphate.

Example 2

An Investigation of the Effect of a Combination of Lactase and Lactic Acid Bacteria on Lactose Digestion in Lactose Malabsorbers An investigation was carried out to compare the effects of lactase, lyophilized lactic acid bacteria and a combination of lactase and lactic acid bacteria on lactose digestion in lactose malabsorbers.

The investigation consisted of a placebo-controlled, randomized, double-blind cross-over study involving twenty four lactose malabsorbing human subjects. Thirty subjects were initially recruited to the study but six were found not to be lactose malabsorbers and the results obtained from these six subjects were therefore excluded from the analysis of the results.

The study comprising an entry examination and five experimental days, separated by 4 wash-out periods of two weeks each. During the study, the participants were asked not to change their dietary habits and to abstain from taking vitamins, minerals and other supplements. At the beginning of each experimental day, after an overnight fast, a first breath sample was taken from each subject. Thereafter each subject ingested one of five test preparations in randomised order.

The test preparations were provided in capsules of identical appearance, of which one per experimental meal was administered to the study participants together with 150 ml milk to which 5 g of lactose was added, resulting in a lactose-fortified milk containing approximately 12.5 g of lactose. The compositions of the five test preparations were as follows:

Preparation (a): Capsule containing $1 \times 10^9$ cfu *Streptococcus thermophilus* plus $1 \times 10^9$ cfu *Lactobacillus delbrückii* ssp. *bulgaricus*.

Preparation (b): containing 3300 FCC acid lactase from *Aspergillus oryzae*
Preparation (c): Capsule containing 9000 FCC acid lactase from *Aspergillus oryzae*
Preparation (d): Capsule containing a combination of 3300 FCC acid lactase plus $1 \times 10^9$ cfu *Streptococcus thermophilus* and $1 \times 10^9$ cfu *Lactobacillus delbrückii* ssp. *bulgaricus* (test preparation a))
Preparation (e): Di-Calcium-Phosphate (placebo).

The lactic acid bacteria in test preparations (a) and (d) were the strains ST-VC 18 and LB-VC18 described in Example 1 and in the description on page 24 above. Test preparation (b) was Lactrase 3300 (Pro Natura Gesellschaft für gesunde Ernährung mbH, Bad Vilbel, Germany), test preparation (c) was Lactrase Plus 9000 (Pro Natura Gesellschaft für gesunde Ernährung mbH, Bad Vilbel, Germany) and test preparation (d) was Lactrase 3300 (Pro Natura) to which the lactic acid bacteria were added.

The randomization of study participants as well as packaging and coding of the test preparations was performed by subjects who were otherwise not involved in the study.

The lactose dose given (12.5 g) was less than for a classic lactose malabsorption test (50 g) but is closer to the lactose-content of normally ingested foodstuffs. In the classic lactose malabsorption test (carried out with 50 g of lactose) $H_2$ peak concentrations of 20 ppm and more are considered to be a proof of lactose malabsorption. However, because of the smaller lactose doses given in the present study, a lower threshold was used to determine whether a participant was a lactose malabsorber. Therefore, participants with $H_2$ peak concentrations of 13 ppm and more with placebo were considered lactose malabsorbers and the results obtained from these participants were included in the study.

The effect of the test preparations on lactose digestion was measured using $H_2$-breath tests which were carried out on a MicroLyzer Model 12i, QuinTron Instruments, Milwaukee, Wis. 53215, USA. Hydrogen gas is released in approximately 90% of the population when carbohydrates are fermented by bacteria in the colon. Therefore, the amount of hydrogen in exhaled breath provides a good indicator of the amount of lactose being fermented in the colon and also constitutes a good indicator of lactase deficiency in the small intestine.

Breath samples were taken for 3 hours. The $H_2$ peak concentration was chosen as a parameter for lactose digestion. The $H_2$ peak concentrations for each of the subjects and each of the five preparations are shown in the table below.

| | $H_2$ Max values | | | | |
|---|---|---|---|---|---|
| Subject ID | Preparation (e) | Preparation (a) | Preparation (b) | Preparation (c) | Preparation (d) |
| 3501 | 27 | 48 | 2 | 16 | 7 |
| 3503 | 15 | 12 | 4 | 2 | 18 |
| 3504 | 37 | 36 | 33 | 46 | 9 |
| 3505 | 27 | 10 | 24 | 16 | 15 |
| 3506 | 27 | 14 | 29 | 35 | 18 |
| 3507 | 48 | 44 | 25 | 14 | 7 |
| 3508 | 18 | 38 | 24 | 23 | 15 |
| 3509 | 22 | 33 | 45 | 27 | 20 |
| 3510 | 33 | 33 | 28 | 33 | 28 |
| 3511 | 29 | 29 | 12 | 45 | 18 |
| 3513 | 13 | 10 | 6 | 4 | 17 |
| 3514 | 17 | 9 | 8 | 10 | 4 |
| 3516 | 15 | 21 | 7 | 10 | 13 |
| 3517 | 34 | 19 | 10 | 3 | 10 |
| 3518 | 15 | 5 | 16 | 22 | 11 |
| 3520 | 15 | 7 | 14 | 10 | 6 |
| 3521 | 27 | 12 | 31 | 5 | 9 |
| 3522 | 13 | 5 | 8 | 2 | 16 |
| 3524 | 21 | 16 | 5 | 3 | 5 |
| 3526 | 26 | 18 | 16 | 16 | 19 |
| 3527 | 19 | 17 | 18 | 16 | 12 |
| 3528 | 22 | 15 | 18 | 12 | 13 |
| 3529 | 45 | 45 | 61 | 24 | 15 |
| 3530 | 53 | 33 | 22 | 39 | 43 |

Statistical analysis of the results of the study showed that there was a significant global effect between the diets with respect to the $H_2$-max values obtained (Friedmann-Test, p=0.001). Multiple comparison (Wilcoxon) showed significant differences with respect to $H_2$-max values between preparation (b), which contains 3300 FCC units of lactase, and the placebo preparation (e), between (c), which contains 9000 FCC units of lactase, and the placebo preparation (e) and between the combination preparation (d), which contains 3300 FCC of lactase plus 2 billion cfu lactic acid bacteria, and the placebo preparation (e). Moreover the mean variation (dispersion) of the $H_2$-max values, i.e. the 25/75%-interquartiles area for preparation (d) was only half as big as the mean variations of the other test preparations (i.e. preparations (a), (b) and (c)).

The results demonstrated that all four preparations containing active ingredient(s); i.e. preparation (a) (bacteria alone), preparation (b) (3300 FCC), preparation (c) (9000 FCC) and preparation (d) (the combination preparation) reduced the $H_2$-breath concentrations in at least some subjects but only the 3300 FCC preparation (preparation (b)), the 9000 FCC preparation (preparation (c)) and the combination preparation (preparation (d)) showed a significant effect. The combination preparation (d) was even more effective than the 9000 FCC-containing preparation (c) and also showed a significantly lower mean variation in the $H_2$-exhalation-values. An analysis of the data showed that fewer participants who received the combination preparation (d) enjoyed little or no beneficial effect. The advantage of the combination preparation (d) was therefore not only its stronger contribution to lactose digestion but also that it was effective in a larger proportion of the study participants. It may therefore be concluded that more lactose malabsorbers would benefit from the lactose digestive effect of combination preparation (d) than would benefit from the individual lactic acid bacteria preparation (a) and the lactase preparations (b) and (c).

Example 3

An Investigation of Lactose Turnover by Incubation of Lactose with *Streptococcus thermophilus* and *Lactobacillus Bulgaricus* Bacteria In this study, the extent of lactose cleavage by lyophilized and resuspended cultures of *Streptococcus thermophilus* and *Lactobacillus bulgaricus* bacteria was investigated.

The strain of *Streptococcus thermophilus* used was *Streptococcus thermophilus* ST-VC18 (deposition number: DSM 23319) and the strain of *Lactobacillus bulgaricus* used was *Lactobacillus delbrueckii* LB-VC18 (deposition number: DSM 23320).

Lyophilisates of both cultures were resuspended in phosphate buffer, Ph 7.3, both separately and in a 1:1 mixture of both bacteria based on colony forming units (cfu). Additionally, investigations were made as to whether the lactase activity in these bacterial preparations is stable in an acidic milieu comparable to the stomach (simulated gastric fluid=SGF). In all cases lactose cleavage was tested in the presence of pancreatic enzymes (Kreon capsules containing, 10 000 units lipase, 8 000 units amylase and 600 units of pancreas protease according to Pharmacopoea Europea and sodium dodecylsulfate) from porcine pancreas containing active pancreas enzymes plus detergent to mimic bile activity (simulated intestinal fluid=SIF). The amount of glucose, as measured enzymatically by the glucose oxidase assay, was taken as a measure for lactose turnover. The glucose oxidase assay was used as described and as referred to in the Sigma Aldrich Chem Co. Data sheet glucose oxidase assay, 1996.

Lyophilized bacteria (1 mg/ml) were resuspended in 1 ml phosphate buffer (0.1 mol/l). lactose (10 mmol/l) and Kreon in a concentration of 2 capsules per liter (recommended intake 1 to 2 capsules per meal) was added and the suspension was incubated for 10 and 30 minutes. In this experiment, the *Lactobacillus bulgaricus* incubation resulted in the liberation of 1.7 mmol/l glucose after 30 minutes and incubation with *Streptococcus thermophilus* yielded 2.8 mmol/l glucose, indicating turnovers of 17 and 28% respectively.

In order to test the acid stability of the lactase activity, resuspended lyophilisates (1 mg/ml bacterial lyophilisate per ml suspension) were incubated with simulated gastric fluid, Ph 4.0, for 10, 30 and 60 minutes. The suspension was neutralized by addition of phosphate buffer to give a Ph of approximately 7.0, and then lactose (10 mmol/l) and Kreon were added and the lactase activity determined as described above (30 min incubation of bacterial suspension with lactose, i.e. identical conditions).

*Lactobacillus* suspensions liberated 2.0 to 2.5 mmol/l glucose after 30 minutes and *Streptococcus* suspensions liberated 3 to 3.5 mmol/l glucose after this period. No difference was seen between the samples having been incubated for 10, 30 or 60 minutes with simulated gastric fluid.

This experiment demonstrates that the lactase activity in both preparations is stable in a reconstituted stomach environment.

In a third experiment *Streptococcus thermophilus* and *Lactobacillus bulgaricus* lyophilisates were mixed on a 1:1 basis (based on the numbers of colony forming units). For turnover measurements, 1 mg *Streptococcus* and 0.6 mg *Lactobacillus* bacteria were resuspended in 1 ml phosphate buffer and the resulting mixture was incubated with simulated intestinal fluid. After incubating this mixture for 30 minutes with 10 mmol/l lactose, 3.1 mmol glucose was detected.

The same mixture was incubated for 30 minutes with simulated gastric fluid prior to lactase determination. After neutralisation and incubation for 30 minutes in simulated intestinal fluid with 10 mmol/l lactose, the concentration of glucose was found to be 3.15 mmol/l thereby demonstrating the stability of this mixture against acidic conditions.

The experiments demonstrate the presence of lactase activity in lyophilized bacteria. This lactase activity is stable and active in simulated intestinal fluid, even after having been subjected to simulated gastric fluid before being tested in SIF. From these experiments it can be concluded that in vivo hydrolysis of lactose in the small intestine can be achieved by ingestion of the combination of both bacteria or by ingestion of each bacteria on its own and that there is no significant difference between the activities of the individual types of bacteria when used alone or when used in combination.

The data provided in the examples above demonstrate that combinations of acid lactase and the bacteria *Streptococcus thermophilus* and/or *Lactobacillus bulgaricus* provide a more effective and more reliable improvement in lactose digestion in lactose-malabsorbing subjects than do compositions containing just the lactase or compositions containing just the bacteria. Furthermore, contrary to the teachings in the prior art documents discussed above, it is possible to present the bacteria in dried form and it is not necessary to coat the bacteria with an enteric coating in order to achieve the desired therapeutic effect.

The invention claimed is:

1. A solid dosage form which is suitable for oral administration and is selected from capsules, tablets, dragees, powders, pellets and granules, wherein the solid dosage form is not coated by an enteric coating and contains a lactase (a) derived from *Aspergillus oryzae* which is stable and active in a pH range of 3 to 6; the term stable meaning that the lactase (a) still has at least 30% of its activity after one hour at 37° C. at a pH in the range from 3 to 6, the lactase being present in an amount of from 2000 to 50,000 FCC units; and contains as lactase-producing or lactase-containing microorganisms, both *Lactobacillus delbrueckii* ssp *bulgaricus* and *Streptococcus thermophilus*, the amounts of *Lactobacillus delbrueckii* ssp *bulgaricus* and *Streptococcus thermophilus* being between 100 million and 200 billion colony forming units; wherein the lactase (a) is other than a lactase derived from the said microorganisms; and wherein the microorganisms are in dried form; and provided that the solid dosage form is other than a solid dosage form containing in combination two or more added herbal extracts together with exogenous lipase and exogenous protease.

2. A solid dosage form according to claim 1 wherein the lactase (a) exhibits peak activity at a pH in the range from 3 to 6.

3. A solid dosage form according to claim 1 wherein the lactase (a) is derived from a microorganism, and the solid dosage form is substantially free of the microorganism from which the lactase is derived.

4. A solid dosage form according to claim 1 wherein the solid dosage form is selected from capsules, tablets and dragees.

5. A solid dosage form according to claim 1 wherein the solid dosage form is in unit dosage form.

6. A solid dosage form according to claim 5 wherein the unit dosage form is a capsule.

7. A solid dosage form according to claim 1 which contains between 2000 and 12000 FCC enzyme units of the lactase (a).

8. A solid dosage form according to claim 1 wherein the composition contains from 100 million to 10 billion colony forming units of *Lactobacillus delbrueckii* ssp *bulgaricus* and from 100 million to 10 billion colony forming units of *Streptococcus thermophilus*.

9. A solid dosage form according to claim 1 which is substantially free of lactose.

10. A solid dosage form according to claim 1 wherein the *Lactobacillus delbrueckii* ssp *bulgaricus* is *Lactobacillus delbrueckii* ssp *bulgaricus* LB-VC 18 (deposition number: DSM 23320).

11. A solid dosage form according to claim 1 wherein the *Streptococcus thermophilus* is *Streptococcus thermophilus* ST-VC18 (deposition number: DSM 23319).

12. A solid dosage form according to claim 1 which contains between 100 million and 10 billion colony forming units of *Lactobacillus delbrueckii* ssp *bulgaricus*.

13. A solid dosage form according to claim 1 which contains between 100 million and 10 billion colony forming units of *Streptococcus thermophilus*.

14. A method for the therapy of lactose intolerance or conditions arising from lactase deficiency, which method comprises administering to a subject in need thereof an effective amount of a composition which is a solid dosage form according to claim 1.

15. A method according to claim 14 wherein the composition is in unit dosage form.

16. A method according to claim 15 wherein the unit dosage form is a capsule.

17. A method according to claim 14 wherein the composition contains between 2000 and 12000 FCC enzyme units of the lactase (a).

18. A method according to claim 14 wherein the effective amount of the composition contains from 100 million to 10 billion colony forming units of *Lactobacillus delbrueckii* ssp *bulgaricus* and from 100 million to 10 billion colony forming units of *Streptococcus thermophilus*.

19. A method according to claim 14 wherein the composition is substantially free of lactose.

20. A method according to claim 14 wherein the *Lactobacillus delbrueckii* ssp *bulgaricus* is *Lactobacillus delbrueckii* ssp *bulgaricus* LB-VC18 (deposition number: DSM 23320).

21. A method according to claim 14 wherein the *Steptococcus thermophilus* is *Streptococcus thermophilus* ST-VC18 (deposition number: DSM 23319).

22. A method according to claim 14 wherein the composition is other than a composition containing in combination two or more added herbal extracts together with exogenous lipase and exogenous protease.

\* \* \* \* \*